(12) United States Patent
Muramatsu (10) Patent No.: US 7,530,280 B2
(45) Date of Patent: May 12, 2009

(54) MICRO ACTUATOR

(75) Inventor: Naoki Muramatsu, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 430 days.

(21) Appl. No.: 10/753,329

(22) Filed: Jan. 9, 2004

(65) Prior Publication Data
US 2004/0159169 A1   Aug. 19, 2004

Related U.S. Application Data (63) Continuation-in-part of application No. 09/581,616, filed as application No. PCT/JP97/04601 on Dec. 15, 1997, now Pat. No. 6,691,586.

(51) Int. Cl.
*F16H 21/00* (2006.01)
*F16H 3/06* (2006.01)
*B25B 9/00* (2006.01)

(52) U.S. Cl. .......................... 74/25; 74/89.23; 294/100; 901/38; 901/39

(58) Field of Classification Search .................. 74/25, 74/89.23, 89.25; 294/99.1, 86.4, 100; 901/23, 901/30, 31, 38, 39, 40, 41, 45; 977/DIG. 1
See application file for complete search history.

(56) References Cited

U.S. PATENT DOCUMENTS

| 3,527,492 | A | * | 9/1970 | Hollis ........................ 294/19.1 |
| 5,458,385 | A | * | 10/1995 | Peeples ....................... 294/19.1 |
| 6,513,213 | B1 | * | 2/2003 | Muramatsu et al. ........ 29/25.35 |
| 7,073,833 | B2 | * | 7/2006 | Muramatsu ................. 294/100 |
| 7,083,210 | B2 | * | 8/2006 | Muramatsu et al. ......... 294/100 |

* cited by examiner

*Primary Examiner*—Richard W L Ridley
*Assistant Examiner*—James Pilkington
(74) *Attorney, Agent, or Firm*—Sughrue Mion, PLLC (57) ABSTRACT

A micro actuator including a translationally driving section having a moving portion which is incorporated in a case and moves translationally, and a displacement enlarging member having one end portion connected to the moving portion of the translationally driving section and another end portion connected to the case, wherein as the one end portion is pulled on the basis of the translational movement, the amount of displacement of its distal end is enlarged.

18 Claims, 12 Drawing Sheets

AMOUNT OF DISPLACEMENT OF DISTAL END PORTION

FIG. 15C

MICRO ACTUATOR

This application is a Continuation-In-Part of U.S. patent application Ser. No. 09/581,616, filed Jun. 15, 2000 now U.S. Pat. No. 6,691,586, which was the National Stage of International Application No. PCT/JP97/04601, filed Dec. 15, 1997.

TECHNICAL FIELD

The present invention relates to a micro actuator, and more particularly to improvements in a micro actuator in which the amount of translational displacement can be easily enlarged.

BACKGROUND ART

There are many micro actuators (hereinafter referred to as actuators) which are in a research-and-development stage, but the number of actuators which have reached the product stage is very small. This is conceivably due partly to the difficulty in the microminiturization of the actuators themselves. In such a situation, Japanese Patent Unexamined Publication No. Hei. 8-90477 is known as the conventional art of the actuator which discloses the basic configuration of a product.

Such an actuator is characterized by a drive mechanism in which the expanding and contracting displacement of a movable frame due to a piezoelectric element is converted to the opening and closing displacement of a U-shaped pair of gripper fingers through a swinging mechanism consisting of a hinge and levers, and there is an advantage in that the pair of gripper fingers exhibits equalized opening and closing behavior with respect to an object to be gripped.

With the above-described conventional actuator, however, to utilize the expanding and contracting displacement of the piezoelectric element as the displacement for actuating the gripper, a mechanism for enlarging the displacement must be provided, so that the structure has been complex. For example, since the expanding and contracting displacement of the piezoelectric element is on the order of nanometers, there has been a problem in that a mechanism for enlargement by a factor of several hundreds is required to obtain an opening and closing displacement of even several hundred microns for the gripper fingers.

DISCLOSURE OF THE INVENTION

The invention has been made to overcome the above-described problems, and its object is to provide an actuator in which the amount of displacement of a distal end portion gets large on the basis of a slight amount of displacement of a driving section without using an enlarging mechanism.

To attain this object, the actuator according to a first aspect is characterized by comprising: a case; a translationally driving section having a moving portion mounted on said case for translational movement; and a displacement enlarging member including a first side portion having a first end portion connected to said case, a second side portion having a second end portion connected to said moving portion of said translationally driving section, and a distal end portion, said first and second side portions respectively extending from said first and second end portions and being in direct contact with each other to form a common portion, wherein as said second end portion is pulled on the basis of the translational movement, an amount of displacement of said distal end portion is enlarged more than an amount of the translational movement and said first side portion is elastically bent, and said first side portion is made of a material that is different from a material of said second side portion.

The actuator according to a second aspect is characterized in that the first side portion has a hole in the vicinity of a distal end thereof, and a distal end of the second side portion is hooked in the hole.

The actuator according to a third aspect is characterized in that a portion of the first side portion is bent to form a substantially L-shaped raised portion that is located in the vicinity of a distal end of the first side portion, a distal end of the second side portion is connected to or engaged with the raised portion, and the second side portion is substantially in parallel with and adjacent to the first side portion.

The actuator according to a fourth aspect is characterized in that the flexibility of the second side portion is different from that of the first side portion.

The actuator according to a fifth aspect is characterized in that the second side portion is made of ceramic, glass, wood or wire.

BEST MODE FOR CARRYING OUT THE INVENTION

Next, a description will be given hereafter of the embodiments of the invention.

First Embodiment

Figure 1A:
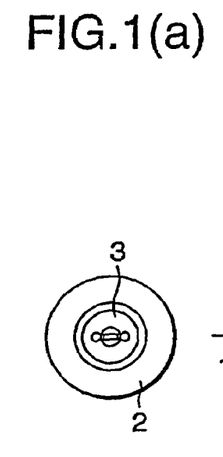
FIG. 1 is cross-sectional views and a side elevational view illustrating an overall actuator according to an embodiment of the invention, in which the part (a) is a side elevational view, the part (b) is a cross-sectional view, and the part (c) is a cross-sectional view taken in the direction of arrows along line C-C in the part (b)
Figure 1B:
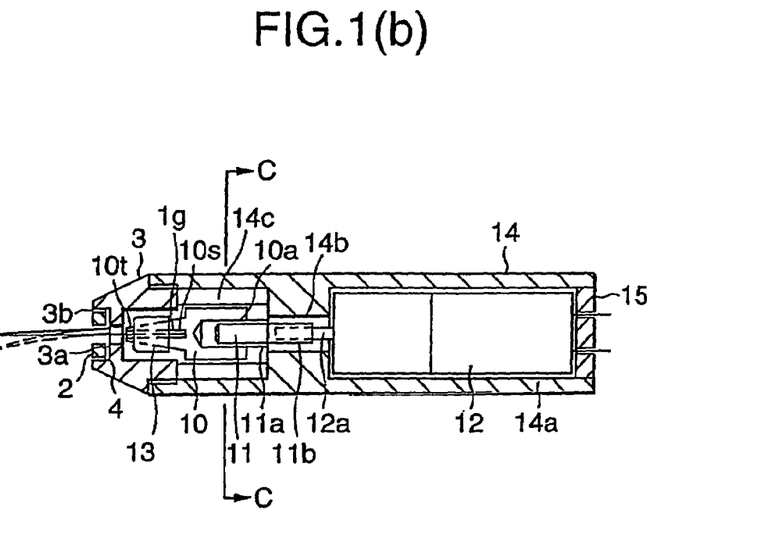
Figure 1C:
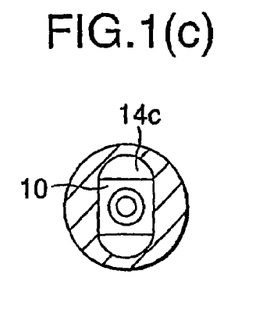
Figure 2:
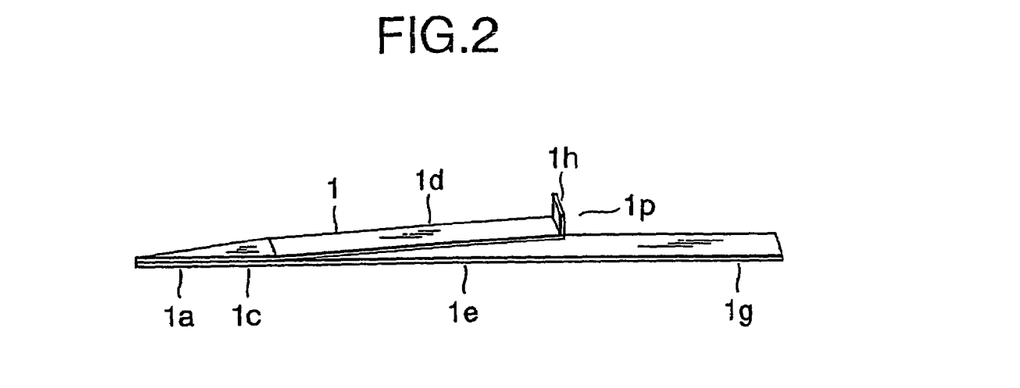
FIG. 2 is a perspective view illustrating an operating finger shown in FIG. 1.

Referring to FIGS. 1 and 2, a description will be given of an embodiment of the invention. FIG. 1 is cross-sectional views and a side elevational view of an actuator, and FIG. 2 is a perspective view of a plate-shaped displacement enlarging member.

In FIGS. 1 and 2, the actuator is comprised of an operating finger 1 serving as a substantially V-shaped displacement enlarging member whose distal end portion undergoes enlarging displacement on the basis of translational displacement so as to operate on a very small object; a drive section for imparting a driving force on the operating finger 1 by rotating; a converting section for converting the rotation of this drive section to translational movement; a connecting section for connecting this converting section and the operating finger 1; a case section for accommodating the converting section, the drive section, and the connecting section; and a fixing section for fixing a portion of the operating finger 1 by making use of the case section.

As shown in FIG. 2, the operating finger 1 includes a common portion 1a which is beam-like and plate-shaped and has distal ends in common in a superposed manner; two side portions 1d and 1e extending from this common portion 1a and opposing each other; an open portion 1p which is located on the side away from the common portion 1a and is open; one end 1g of the open portion; and a hook-like leg 1h thereof. It should be noted that the common portion (distal end portion) 1a of the operating finger 1 acts on the object.

Here, a metallic material having a spring characteristic is used for the operating finger 1, and a secured portion 1c, in which the side portion 1d and the side portion 1e are secured together by means of soldering, welding, an adhesive agent, or the like, is formed in the common portion 1a. It should be noted that, instead of the metallic material, a nonmetallic material such as a resin may be used depending on the object.

The drive section is, for example, a coreless dc motor (hereafter referred to as motor) 12 with a reducing gear having a rotor shaft 12a which is connected to the end 1g of the operating finger 1 through the converting section so as to cause the end 1g to undergo translational displacement. Where the, drive section and the convening section together form a translationally driving section.

The converting section includes a threaded shaft 11 having a thread 11a on its outer periphery and having a hollow portion 11b in which the rotor shaft 12a of the motor 12 is fitted and fixed, as well as a nut 10 having a thread 10a on a peripheral surface of a hollow portion formed by cutting its rear end, the thread 11a of the threaded shaft 11 being threadedly engaged with the thread 10a. The converting section is arranged in such a manner as to convert the rotation of the rotor shaft 12a of the motor 12 to translational displacement of the nut 10. Where the nut 10, being translationally displaced through the threaded shaft 11, is a moving portion of the translationally driving section. As shown in FIGS. 1(b and c), the nut may have the shape of a quadrangular prism.

The connecting section includes a substantially conically shaped conical portion in which a tapered screw lot is formed on an outer peripheral portion of a distal-end projection of the nut 10, as well as a tapered nut 13 for being threadedly engaged with the tapered screw 10t. A slit 10s is provided in the center of the conical portion of the nut 10, the end 1g of the operating finger 1 is inserted in this slit 10s, and the tapered nut 13 is threadedly engaged with the tapered screw 10t, thereby connecting and fixing the end 1g of the operating finger 1.

The case section is formed by a case 14, a cover 15 for closing a right-hand end face of the case 14, and a cap 3 which is engaged with and fixed to a left-hand end face of the case 14.

The case 14 includes a motor accommodating portion 14a formed in a hollow cylindrical shape for accommodating the motor 12 in its cylindrical space portion, a threaded-shaft accommodating portion 14b for accommodating the rotor shaft 12a of the motor 12 and a portion of the threaded shaft 11, and a nut accommodating portion 14c for accommodating the nut 10 and serving as a guide portion formed such that its entire portion is oval and its end portions are substantially semicircular, as shown in the C-C cross-sectional view of FIG. 1.

The cap 3 has a hollow cylinder in which the connecting section is contained and which has a tubular shape with a cross section formed in a substantially trapezoidal shape and has a two-staged through hole in its center. A flange 3a is provided such that an end face of this hollow cylinder is formed in a recessed shape, and a thread 3b is provided on the peripheral surface of the recessed portion.

The fixing section fixes the leg 1h of the operating finger 1 to the cap 3 as the leg 1h of the operating finger 1 abuts against the flange 3a of the cap 3 with a washer 4 interposed therebetween and a thread formed on the outer peripheral surface of a holder 2 is threadedly engaged with the thread 3b of the recessed portion of the cap 3.

In the above-described configuration of the actuator, a description will be given hereafter of the enlargement and displacement of the distal end of the operating finger 1 on the basis of the rotational displacement of the rotor shaft 12a of the motor 12. Consideration will be given by using a model in which, as shown in FIG. 3, the end of the operating finger 1 is pulled by a load P with the hook-like leg 1h of the operating finger 1 fixed (at the point 0 in FIG. 3) on X and Y axes.

Figure 3:
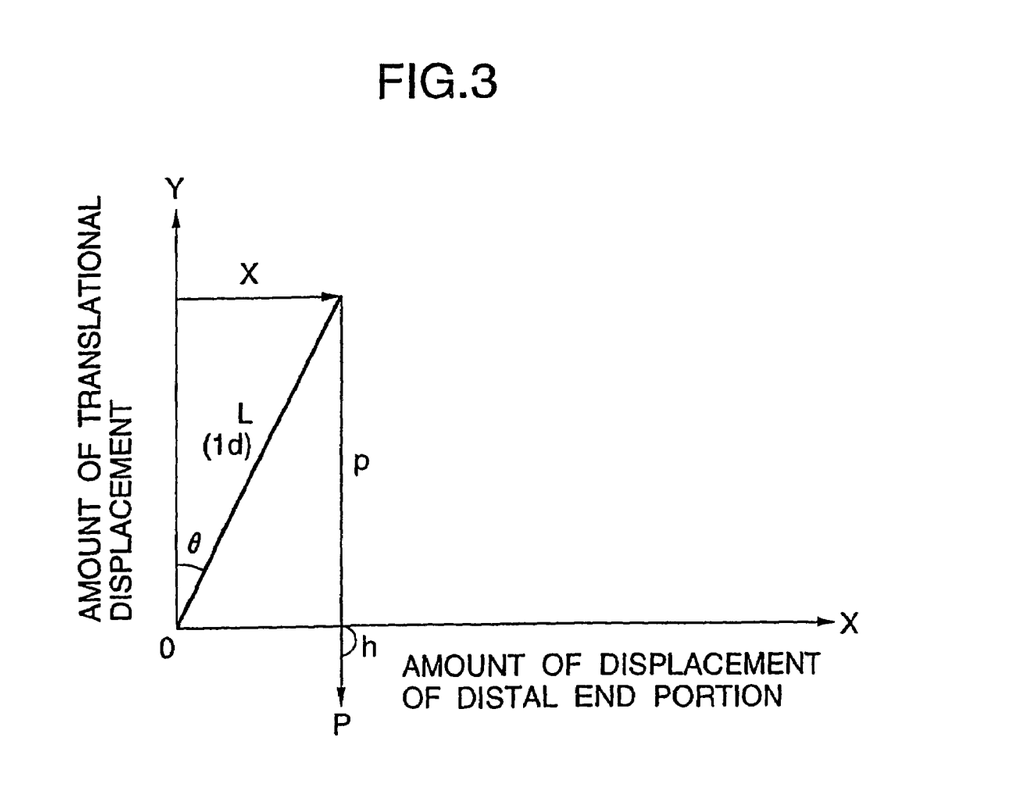
FIG. 3 is a model diagram explaining the amount of displacement of a distal end portion of the operating finger shown in FIG. 1.

In FIG. 3, if the rate of displacement, X, in the X-axis direction of the operating finger 1 with respect to a slight amount of translational displacement, h, in the X-axis direction of the end of the operating finger 1 (hereafter, the rate of this displacement will be referred to as the amount of displacement of the distal end portion) is assumed to be an enlargement rate G=X/h, the amount of displacement, X, of the distal end portion, the amount of translational displacement, h, and the enlargement rate G can be expressed by formulae shown below. Incidentally, it is assumed that the beam L does not bend and that $\Theta$ is infinitesimal.

$$X = L \sin \Theta \approx L\Theta$$

$$h = L(1-\cos \Theta) \approx L(\Theta^2/2)$$

$$G = X/h = 2/\Theta$$

Specifically, if it is assumed that the amount of translational displacement, h, of the operating finger 1 is 0 to 10° in terms of the angle $\Theta$, the enlargement rate G becomes $\infty$ to 11.5. Namely, the amount of displacement, X, of the distal end portion is enlarged with respect to a slight amount of translational displacement, h.

For example, as a result of an experiment conducted by using as the operating finger 1 a phosphor bronze sheet for a spring having a thickness of 0.1 mm, a width of 2 mm, and a length of 30 mm, the amount of displacement, X, of the distal end portion was X=8.5 mm with respect to an amount of translational displacement, h, of 1 mm, and the tensile force P for forced displacement was 60 g or thereabouts.

In addition, to make the apparatus more compact, it is possible to make use of a buckling phenomenon, for example. The buckling phenomenon referred to herein means the phenomenon in which when an applied load reaches a certain value, transverse displacement quickly occurs. Namely, by causing the end of the operating finger 1 to be translationally displaced, the distal end of the operating finger 1 is quickly displaced.

To obtain such a buckling phenomenon, the hook-like leg 1h of the operating finger 1 and the other leg 1g thereof are arranged to be disposed in very close proximity to each other. That is, as described above, since the leg 1h of the operating finger 1 is held onto the flange 3a with the washer 4 interposed therebetween by means of the holder 2, it suffices if the amount of the tightening allowance of the leg 1h is adjusted so as to obtain the buckling phenomenon.

Figure 4:
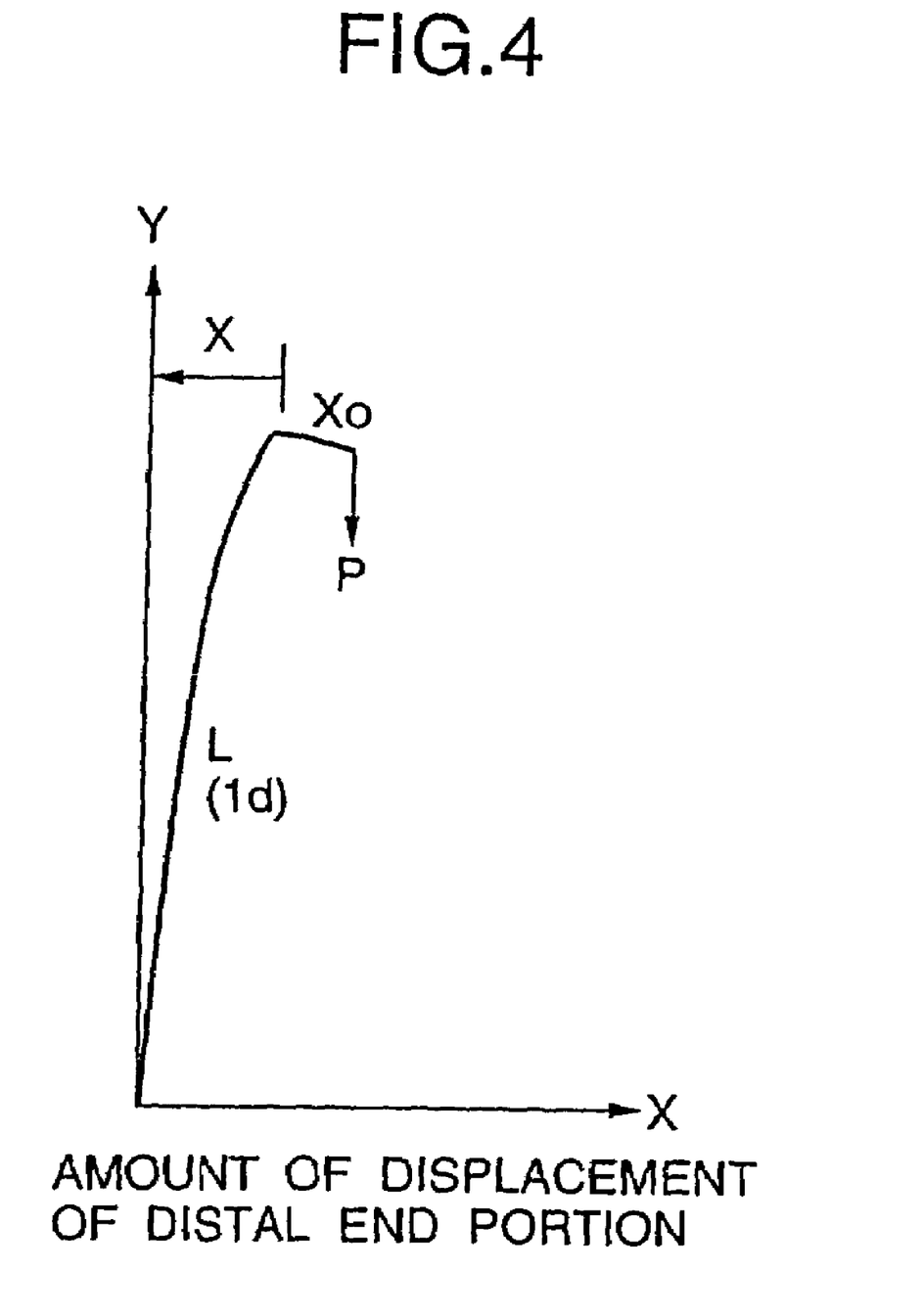
FIG. 4 is a model diagram in which the distal end portion of the operating finger shown in FIG. 3 is enlarged.

In such a configuration, from FIG. 4 which makes clearer the distal end portion of the model shown in FIG. 3, the relation between the load P and the amount of displacement, X, of the distal end portion is expressed by the formula shown below. It should be noted, however, that $X_0$ is the amount of eccentric displacement of the load P.

$$P=(EI/L^2)\{\cos^{-1}(X_0/(X+Y_0))\}^2 \quad (1)$$

where E is the modulus of longitudinal elasticity (kg/mm$^2$), and I is the moment of inertia of area (mm$^2$).

Here, if it is assumed that $X_0 \approx 0$, we have $$\cos^{-1}X_0/(X+X_0) \approx \pi/2$$

Figure 5:
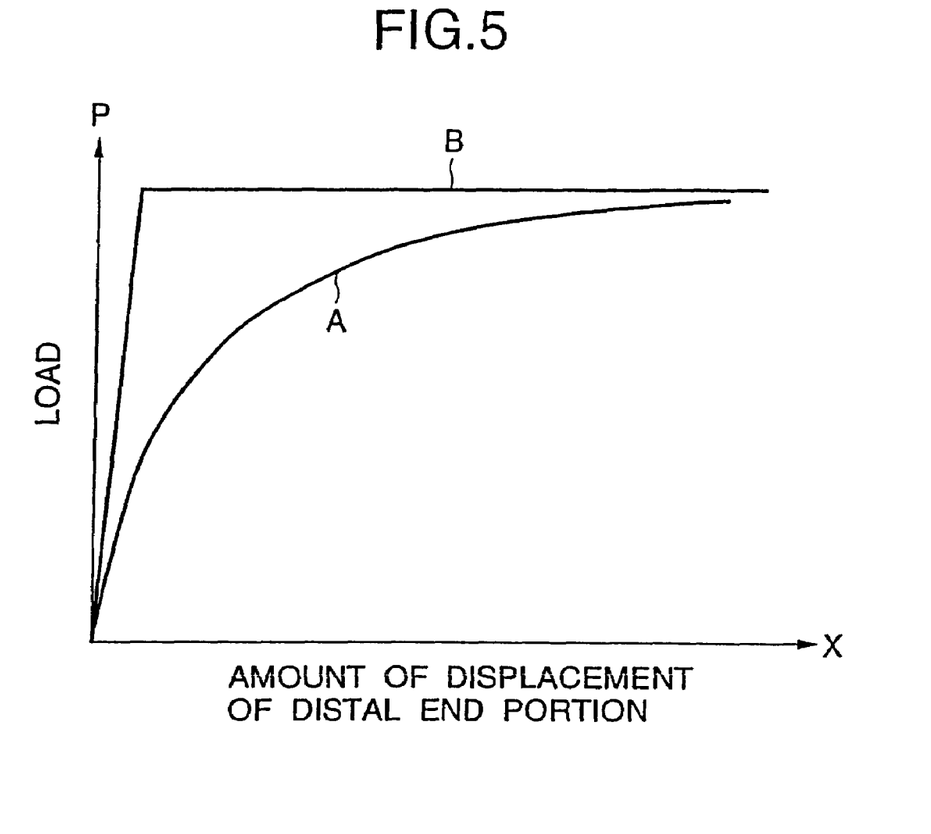
FIG. 5 is a graph illustrating the load on the operating finger and the amount of displacement of the distal end portion in FIG. 1.

As a result, the load P becomes fixed at $(EI^2\pi)/(4L^2)$ irrespective of the amount of displacement, $X_0$, as shown by a curve B in FIG. 5.

Next, mainly referring to FIG. 1, a description will be given of the operation of the actuator configured as described above. First, a power supply is turned on for the motor 12, and the rotor shaft 12a of the motor 12 rotates. This rotation causes the nut 10 to be translationally displaced in the rightward direction in FIG. 1 through the threaded shaft 11. This translational displacement is transmitted to the nut 10 through the threaded shaft 11, and the nut 10 slides in the nut accommodating portion 14c and is displaced in the rightward direction in FIG. 1 with respect to the axis of the threaded shaft 11.

Concurrently, the end 1g of the operating finger 1 is forcefully displaced with the same amount of displacement and in the same direction (in the direction in which it is pulled by the rotor shaft 12a of the motor 12), and bending moment is applied to the operating finger 1, so that the operating finger 1 is bent from the direction indicated by the solid line toward the direction indicated by the broken line, as shown in FIG. 1. Here, if the operating finger 1 has a normal bending characteristic, the operating finger 1 exhibits the displacement characteristic such as the one shown by a curve A in FIG. 5, but if the operating finger 1 is arranged to display a buckling phenomenon, the operating finger 1 exhibits the displacement characteristic such as the one shown by the curve B in FIG. 5. This enlarging/bending displacement is made to act on the object.

On the other hand, if the rotation of the rotor shaft 12a of the motor 12 is reversed, the rotation causes the nut 10 to be translationally displaced in the leftward direction in FIG. 1 through the threaded shaft 11. This translational displacement is transmitted to the nut 10 through the threaded shaft 11, and the nut 10 is displaced in the nut accommodating portion 14c in the axial direction. As this translational displacement is transmitted in the same way as described above and causes the bending displacement of the operating finger 1 to be canceled, and the distal end portion of the operating finger 1 is returned as indicated by the solid lines in FIG. 1.

In addition, although not shown, the common portion 1a of the operating finger 1 in FIG. 2 may be located away from the distal end. According to such a configuration, since the common portion 1a ceases to be present at the distal end of the operating finger 1, the thickness of the distal end of the operating finger 1 can be made thin, and the amount of enlarging displacement can be easily adjusted by the position where the common portion 1a is formed.

It should be noted that, as for the converting section, the rotor shaft 12a of the motor 12 where the thread is formed may be directly threadedly engaged with the nut 10. In addition, although the leg 1h of the operating finger 1 is fixed to the cap 3, the leg 1h of the operating finger 1 may not be necessarily fixed to the cap 3, and it suffices if it is fixed to the vicinity of the end 1g of the operating finger 1. Furthermore, the secured portion 1c of the operating finger 1 is not necessarily required in the light of the repeated strength and the like.

Second Embodiment

Figure 6:
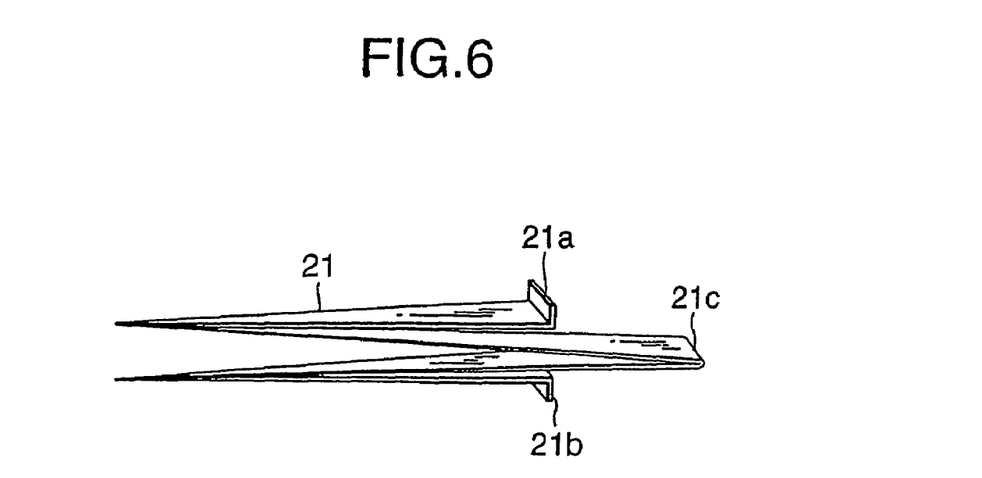
FIG. 6 is a perspective view illustrating a pair of gripper fingers of the actuator according to another embodiment of the invention.
Figure 7:
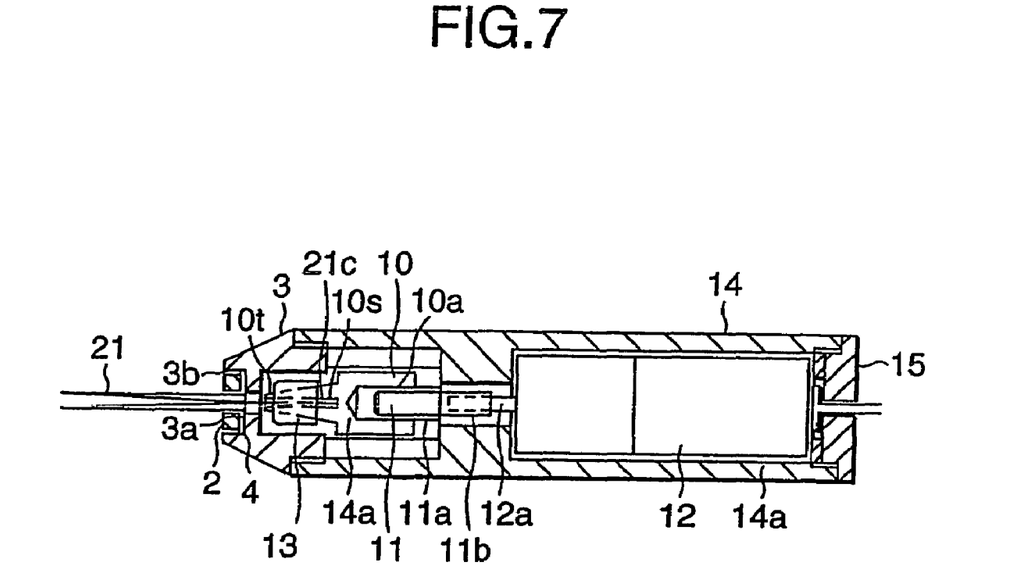
FIG. 7 is a cross-sectional view illustrating the overall gripper fingers shown in FIG. 6.

Referring to FIGS. 6 and 7, a description will be given of another embodiment of the invention. FIG. 6 is a perspective view of the displacement enlarging member having a nipping portion, and FIG. 7 is a cross-sectional view of the actuator having the nipping portion. In the drawings, the same reference numerals as those of FIG. 1 denote identical or corresponding portions, and a description thereof will be omitted.

In FIGS. 6 and 7, this actuator differs from that of FIG. 1 only in the displacement enlarging member, the connecting section, and the fixing section, so that a description will be given of such arrangements. First, a pair of gripper fingers 21 serving as the displacement enlarging member is made of a beam-like member formed substantially in an M-shape and having a spring characteristic. The pair of gripper fingers 21 is formed just as if the ends 1g of two operating fingers 1, one being shown in FIG. 2, are integrated in common, an apex portion 21c is provided in common, and hook-like legs 21a and 21b are respectively provided at ends of the open portions.

The connecting section is arranged such that the apex portion 21c of the gripper fingers 21 is inserted into the slit 10s of the nut 10, and the tapered nut 13 is threadedly engaged with the tapered screw 1ot, thereby joining and fixing the apex portion 21c of the gripper fingers 21.

The fixing section is arranged such that the legs 21a and 21b of the gripper fingers 21 are made to abut against the flange 3a of the cap 3 with the washer 4 interposed therebetween, and the thread formed on the outer peripheral surface of the holder 2 is threadedly engaged with the thread 3b of the recessed portion of the cap 3, thereby fixing the legs 21a and 21b of the gripper fingers 21 to the cap 3.

Referring to FIG. 7, a description will be given of the operation of the actuator configured as described above. First, if the power supply is turned on for the motor 12, the rotor shaft 12a of the motor 12 rotates, and this rotation is transmitted to the nut 10 through the threaded shaft 11, causing the nut 10 to be displaced inside the nut accommodating portion 14c in the rightward direction in FIG. 1 with respect to the threaded shaft 11.

Concurrently, the apex portion 21c of the gripper fingers 21 is forcefully displaced with the same amount of displacement and in the same direction, and bending moment is applied to the gripper fingers 21, so that its distal end portions are bent in mutually approaching directions and are closed to grip the object.

Meanwhile, if the rotation of the motor 12 is reversed, the rotation causes the nut 10 to be translationally displaced in the opposite direction through the threaded shaft 11. This translational displacement is transmitted in the same way as described above and causes the apex portion 21c of the gripper fingers 21 to be translationally displaced, thereby causing the distal end portions of the operating fingers 21 to release the gripping of the object.

Figure 8A:
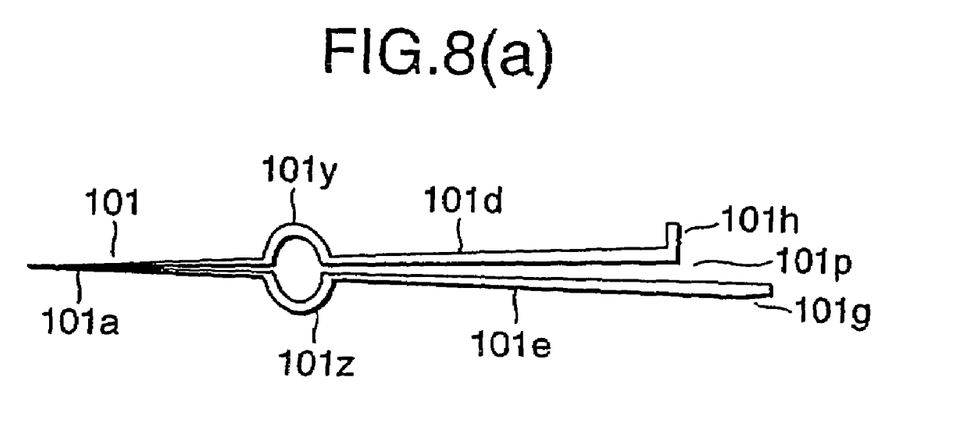
FIG. 8 is a perspective view of the operating finger and the pair of gripper fingers according to the other embodiment of the invention.
Figure 8B:
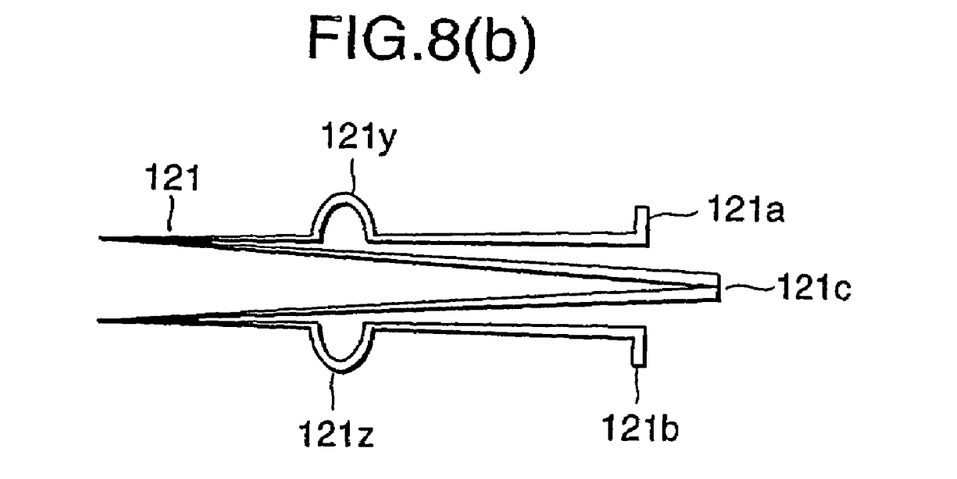

In addition, as shown in FIG. 8, an arrangement may be provided such that semicircular projecting portions 101y and 101z or 121y and 121z which project to the outer sides are provided on side portions of an operating finger 101 and a pair of gripper fingers 121, respectively. According to such an arrangement, the aforementioned enlargement rate G can be varied by the projecting portion 101y and the like, so that a desired displacement of the distal end portion can be easily realized. It should be noted that the kind of shape is not particularly limited and may be a substantially triangular shape, a semielliptical shape, and a semioval shape, and either one of the projecting portions 101y and 101z may be used.

Figure 9A:
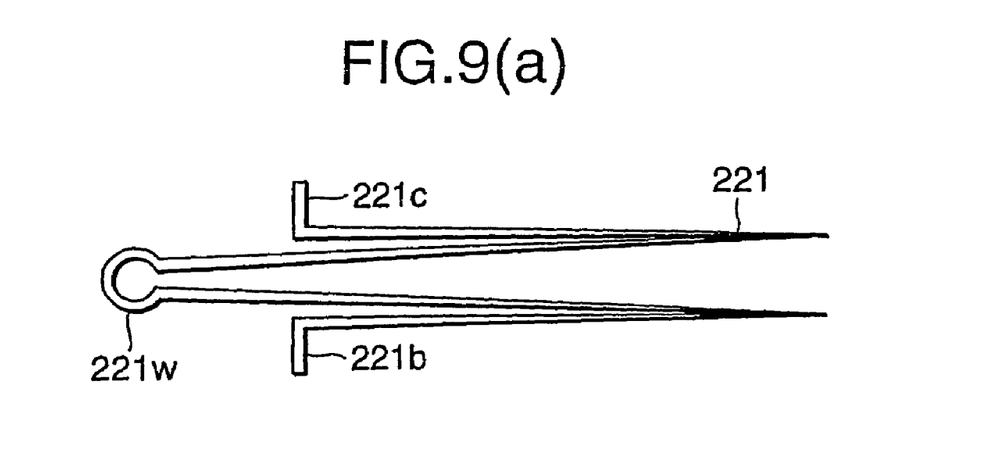
FIG. 9 is a perspective view of the operating finger and the pair of gripper fingers according to the other embodiment of the invention.
Figure 9B:
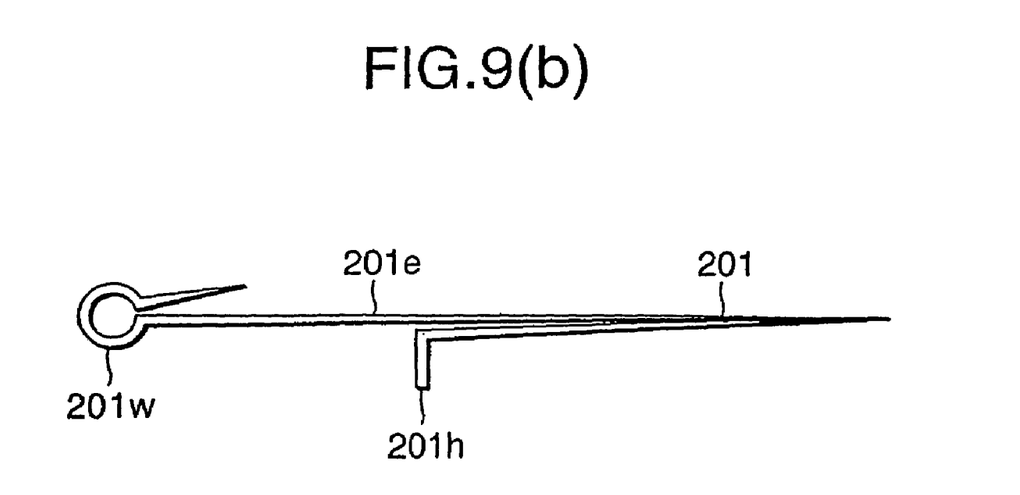
Figure 10:
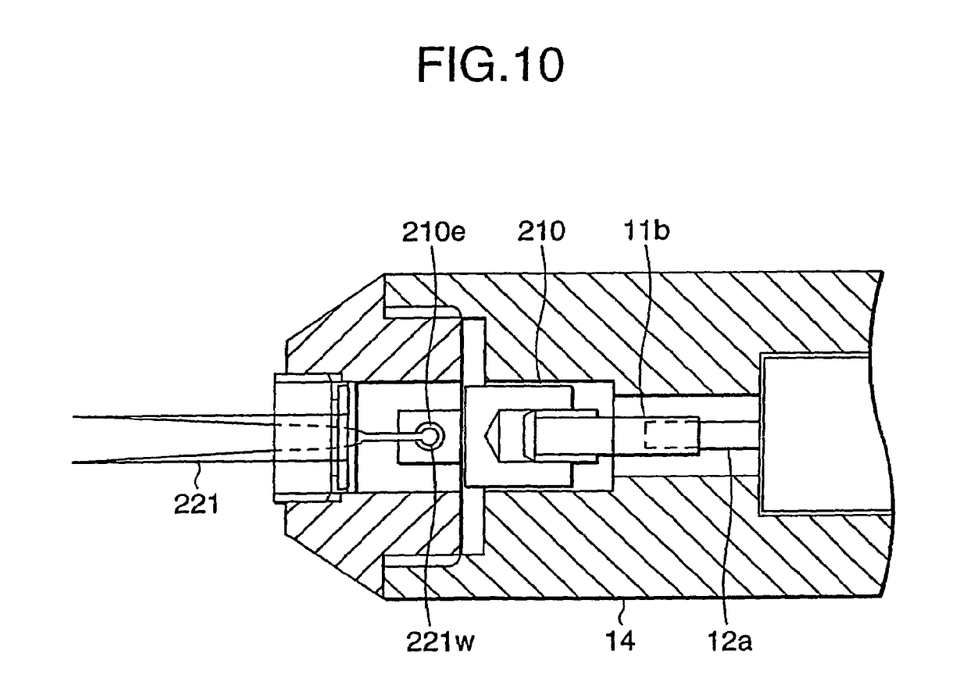
FIG. 10 is a cross-sectional view in which the pair of gripper fingers shown in FIG. 9 is engaged in a connecting section.

In addition, as shown in FIGS. 9 and 10, an arrangement may be provided such that circular portions 201w and 221w, which are formed in substantially circular shapes, are provided on end portions of an operating finger 201 and a pair of gripper fingers 221, respectively, while a groove 210e to which this circular portion is engaged is provided in a nut 210. According to such an arrangement, the circular portions 201w and 221w of the operating finger 201 and the gripper fingers 221 can be easily engaged and fixed in the groove 210e of the nut 210 or can be removed therefrom.

Third Embodiment

Figure 11:
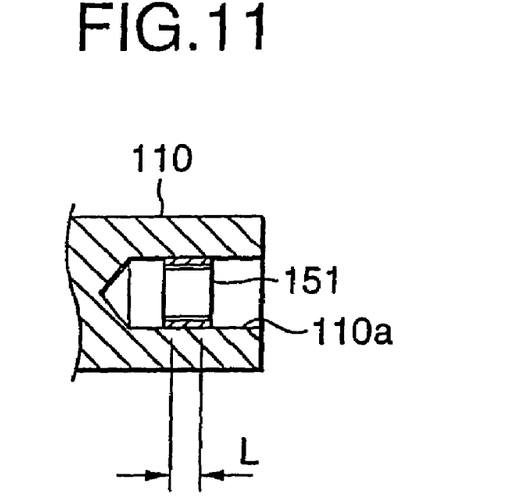
FIG. 11 is a cross-sectional view of a nut of a converting section according to still another embodiment of the invention.
Figure 12:
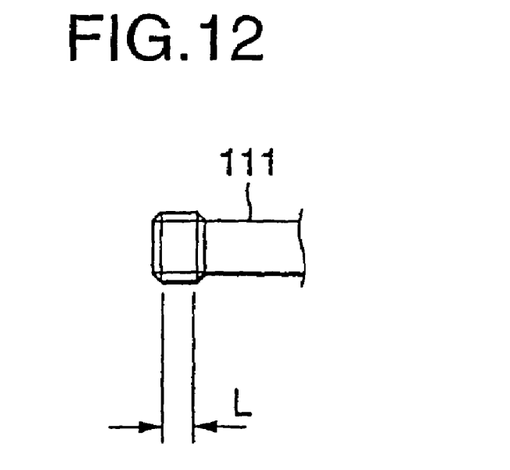
FIG. 12 is a cross-sectional view illustrating a threaded shaft of the converting section according to the still other embodiment of the invention.

Referring to FIGS. 11 and 12, a description will be given of still another embodiment of the invention. FIG. 11 is a cross-sectional view of the nut, and FIG. 12 is a perspective view of the threaded shaft which is threadedly engaged with the nut shown in FIG. 11. In this actuator, only the nut 10 and the threaded shaft 11 shown in FIG. 1 are different, and a translational-displacement-amount limiting portion is provided to limit the amount of the translational displacement of the operating (gripper) finger(s).

In FIGS. 11 and 12, the translational-displacement-amount limiting portion consists of a nut 110 and a threaded shaft 111 serving as a transmitting member which is threadedly engaged with the nut 110. The nut 110 has in its cut hollow portion 110a of a substantially cylindrical shape a limiting nut 151 which is engaged and fixed there in for limiting the translational movement. The limiting nut 151 with an internal thread formed therein as well as the threaded shaft 111 are formed with effective thread length L, and this effective thread length L substantially agrees with a maximum value of the amount of the translational displacement of the finger.

Referring to FIGS. 1, 11, and 12, a description will be given of the operation of the actuator configured as described above. If the motor 12 is driven in the same way as the first embodiment and the threaded shaft 111 is driven by a predetermined number of revolutions or more, the limiting nut 151 is disengaged from the threaded shaft 111 and idles, so that the nut 110 is not translationally displaced any further. Namely, as the threaded shaft 111 is rotated forwardly or reversely, the operating finger 1 is driven only within the amount of translational displacement of the effective thread length L.

It should be noted that although, in the above-described embodiment, the limiting nut 151 is threadedly engaged with the threaded shaft 111, an arrangement may be provided such that the rotor shaft 12a of the motor 12 is elongated and a thread is formed on its outer periphery, and the limiting nut 151 and the rotor shaft 12a may be threadedly engaged with each other.

Fourth Embodiment

Figure 13A:
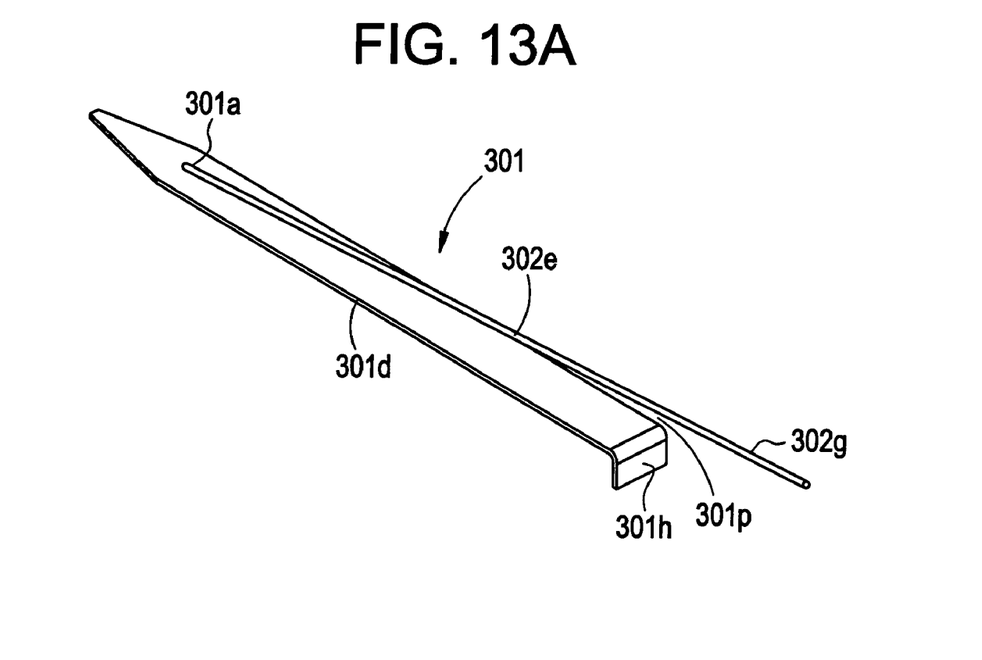
FIG. 13 is a perspective view and a side elevational view illustrating an overall actuator according to still another embodiment of the invention, in which the part (a) is a perspective view, and the part (b) is a side elevational view.
Figure 13B:
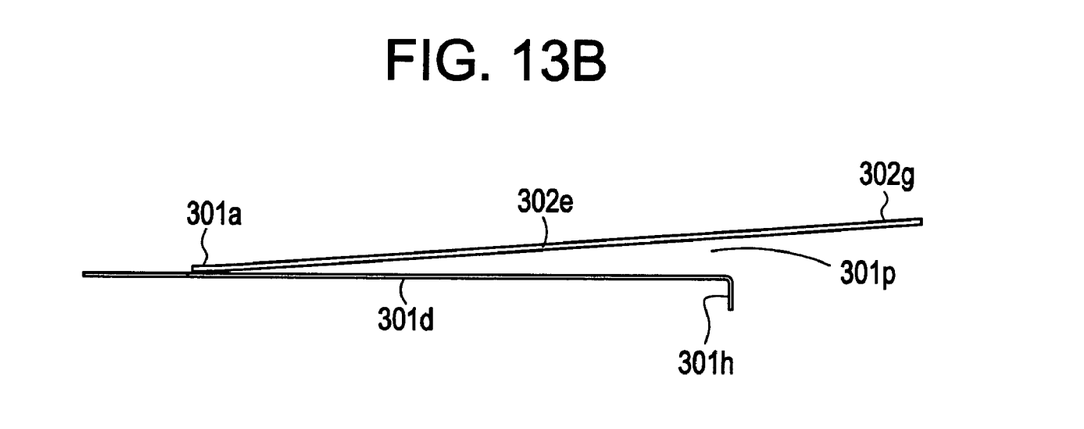

Referring to FIG. 13, a description will be given of a displacement enlarging member according to still another embodiment of the invention. FIG. 13(a) shows a perspective view and FIG. 13(b) shows a side elevational view of the displacement enlarging member. As shown in FIG. 13, an operating finger 301, which serves as a displacement enlarging member, includes: a common portion 301a located slightly away from a distal end and being constructed in a superposed manner; first and second side portions 301d and 302e extending from the common portion 301a and opposing each other; an open portion 301p which is located on the side away from the common portion 301a and is open. The first side portion 301d has on one end thereof a hook-like leg 301h which is connected to and fixed to the case and which serves as a first end portion. The second side portion 302e has a second end portion 302g.

The common portion 301a of the operating finger 301 is located slightly away from a distal end of the first side portion 301d and located centrally in the short side direction (width direction). The common portion 301a is formed by securing a distal end of the second side portion 302e using an adhesive agent, etc.

A metallic material having a spring characteristic and being beam-like plate that has a long side and a short side is used for the first side portion 301d of the operating finger 301. A material having a substantially cylindrical shape is used for the second side portion. For example, ceramic, the modulus of elasticity of which is higher than that of metal, may be used for the material of the second side portion 302e. Also, glass, wood or wire, the modulus of elasticity of which are lower than that of metal, maybe used for the second side portion 302e. Thus, in the operating finger 301, the first side portion 301d is elastically bent. The modulus of elasticity of the first side portion 301d is different from that of the second side portion 302e. That is, the material of the first side portion 301d is different from that of the second side portion 302e.

It should be noted that, a rigid body has an infinite modulus of elasticity, and therefore the rigid body has a modulus of elasticity.

According to the thus structured operating finger 301, although the material of the first side portion 301d is different from that of the second side portion 301e, since the amount of displacement of the distal end portion of the displacement enlarging member 301 becomes large on the basis of a slight amount of translational displacement, there is an advantage in that a simple mechanism can be used without requiring an enlarging mechanism.

Also, since the distal ends of the first and second side portions are not superposed, there is an advantage in that the distal end portion of the displacement enlarging member 301 can be made thin. Therefore, this micro actuator is preferably applicable to a case of gripping an object to be gripped which is placed in a small gap, for example.

Fifth Embodiment

Figure 14B:
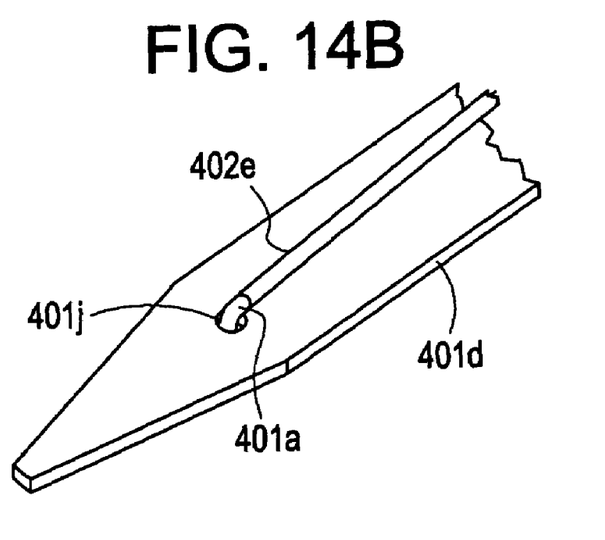
FIG. 14 is a perspective views illustrating an overall actuator according to still other embodiment of the invention, in which the part (a) is a perspective view, the part (b) is an enlarged perspective view, and the part (c) is an enlarged bottom perspective view.
Figure 14C:
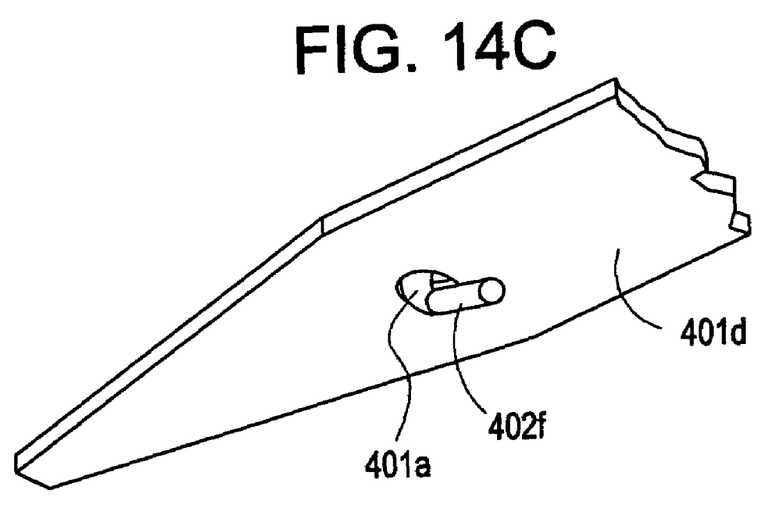

Referring to FIG. 14, a description will be given of a displacement enlarging member according to still other embodiment of the invention. FIG. 14(a) shows a perspective view, FIG. 14(b) shows an enlarged perspective view, and FIG. 14(c) shows a bottom perspective view of the displacement enlarging member.

As shown in FIG. 14, an operating finger 401, which serves as a displacement enlarging member, includes: a common portion 401a located slightly away from a distal end and being constructed in a superposed manner; first and second side portions 401d and 402e extending from the common portion 401a and opposing each other; an open portion 401p which is located on the side away from the common portion 401a and is open. The first side portion 401d has on one end thereof a hook-like leg 401h which is connected to and fixed to the case and which serves as a first end portion. The second side portion 402e has a second end portion 402g.

A metallic material having a spring characteristic and being beam-like is used for the first side portion 401d of the operating finger 401. A hole 401j is formed in the first side portion 401d. The hole 401j is located slightly away from a distal end of the first side portion and located centrally in the width direction. A substantially cylindrical wire is used for the second side portion 402e. A hook 402f formed on a distal end of the second side portion 402e is engaged with the hole 401j of the first side portion 401d to form the common portion 401a.

According to the thus structured operating finger 401, in addition to the advantage obtained by the fourth embodiment, since the displacement enlarging member 401 can be assembled by simply engaging the hook 402f on the distal end of the second side portion 402e with the hole 401j provided in the vicinity of the distal end of the first side portion 401d, the displacement enlarging member 401 can be easily manufactured.

Sixth Embodiment

Figure 15A:
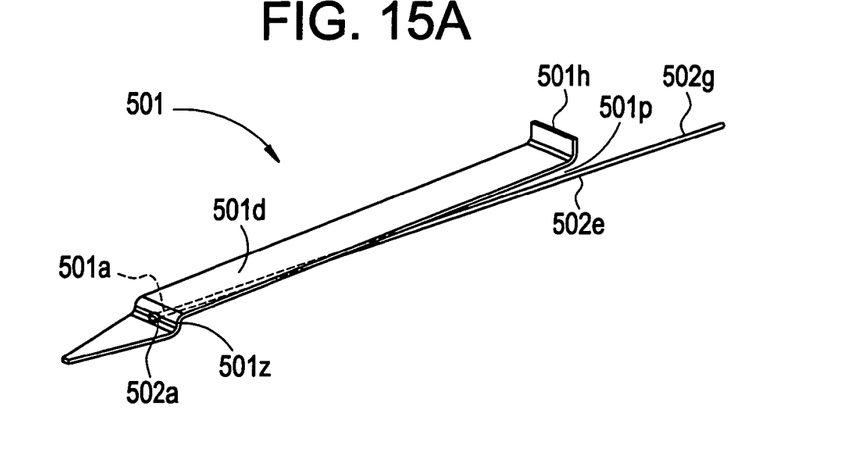
FIG. 15 is a perspective views illustrating an overall actuator according to still another embodiment of the invention, in which the part (a) is a perspective view, the part (b) is an enlarged perspective view, and the part (c) is an enlarged bottom perspective view.
Figure 15B:
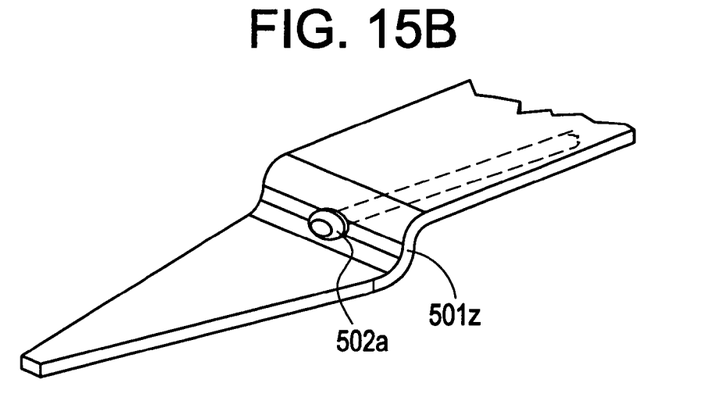
Figure 15C:
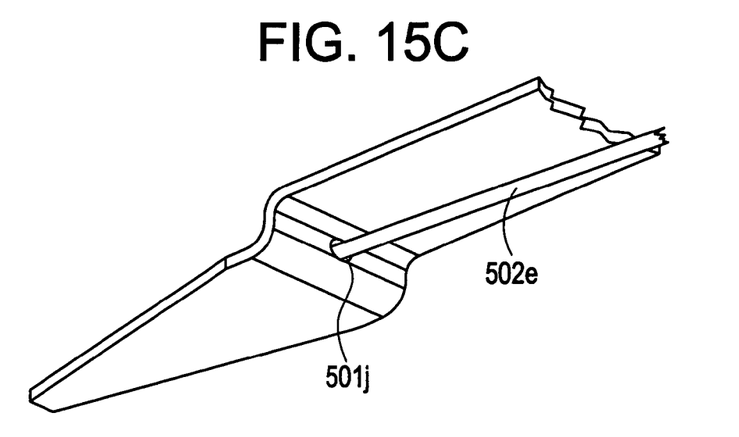

Referring to FIG. 15, a description will be given of a displacement enlarging member according to still another embodiment of the invention. FIG. 15(a) shows a perspective view, FIG. 15(b) shows an enlarged perspective view, and FIG. 15(c) shows a bottom perspective view of the displacement enlarging member.

As shown in FIG. 15, an operating finger 501, which serves as a displacement enlarging member, includes: a common portion 501a located slightly away from a distal end; a first side portion 501d and a second side portion 502e extending from the common portion 501a and opposing each other, the second side portion 502e being spoke-like and having a flange portion 502a; an open portion 501p which is located on the side away from the common portion 501a and is open. The first side portion 501d has on one end thereof a hook-like leg 501h which is connected to and fixed to the case and which serves as a first end portion. The second side portion 502e has a second end portion 502g.

A metallic material having a spring characteristic and being beam-like is used for the first side portion 501d of the operating finger 501. The first side portion 501d has a substantially L-shaped raised portion 501z which is formed by bending a portion in the vicinity of a distal end of the first side portion 501d. A hole 501j located centrally in the width direction is formed in the raised portion 501z. A distal end of the second side portion 502e is engaged with the hole 501j and the second side portion is arranged adjacent to and substantially in parallel with the first side portion 501d.

In this embodiment, the distal end of the second side portion 502e is engaged with the hole 501j of the first side portion 501d. Instead, the distal end of the second side portion 502e may be connected to (fixed to) the raised portion 501z without forming the hole 501j.

According to the thus structured operating finger 501, since the distal end of the second side portion 502e is connected to or engaged with the raised portion 501z provided in the first side portion 501d and the second side portion 502e is adjacent to and substantially in parallel with the first side portion 501d, the displacement enlarging member 501 can be easily manufactured. Also, there is an advantage in that the adjusting operation of the first and second side portions 501d and 502e in the manufacturing process becomes easy.

As described above, according to a first aspect of the invention, since the amount of displacement of the distal end portion of the displacement enlarging member becomes large on the basis of a slight amount of translational displacement, there is an advantage in that a simple mechanism can be used without requiring an enlarging mechanism. Also, there is an advantage in that the first side portion can be made of a material that is different from a material of the second side portion.

According to a second aspect of the invention, since the displacement enlarging member can be assembled by simply engaging the distal end of the second side portion with the hole provided in the vicinity of the distal end of the first side portion, the displacement enlarging member can be easily manufactured.

According to a third aspect of the invention, since the distal end of the second side portion is connected to or engaged with the raised portion provided in the first side portion and the second side portion is substantially in parallel with and adjacent to the first side portion, the displacement enlarging member can be easily manufactured. Also, there is an advantage in that the adjusting operation of the first and second side portions in the manufacturing process becomes easy.

According to fourth and fifth aspects of the invention, there is an advantage in that the first side portion can be made of a material that is different from a material of the second side portion.

INDUSTRIAL APPLICABILITY

As described above, the micro actuator according to the invention is suitable for use in enlargement of the amount of its translational displacement.

What is claimed is:

1. A micro actuator comprising:
   a case;
   a translationally driving section having a moving portion mounted on said case for translational movement; and
   a displacement enlarging member including a first side portion having a first end portion connected to said case, a second side portion having a second end portion connected to said moving portion of said translationally driving section, and a distal end portion, said first and second side portions respectively extending from said first and second end portions and being in direct contact with each other to form a common portion,
   wherein the second side portion is provided in proximity to the first side portion, wherein said first and second side portions extend in a moving direction of said moving portion in a relaxed position, and an entire portion of said first side portion, that extends from said common portion to said first end portion, is straight in the relaxed position, wherein, as said second end portion is pulled on the basis of the translational movement, an amount of displacement of said distal end portion is enlarged more than an amount of the translational movement by a buckling phenomenon and said first side portion is elastically bent, and said first side portion is made of a material that is different from a material of said second side portion.

2. The micro actuator according to claim 1, wherein a portion of said first side portion is bent to form a substantially L-shaped raised portion that is located in the vicinity of a distal end of said first side portion, a distal end of said second side portion is connected to or engaged with said raised portion, and said second side portion is substantially in parallel with and adjacent to said first side portion.

3. The micro actuator according to claim 2, wherein said second side portion is made of ceramic.

4. The micro actuator according to claim 2, wherein said second side portion is made of glass.

5. The micro actuator according to claim 2, wherein said second side portion is made of wood.

6. The micro actuator according to claim 2, wherein said second side portion is made of wire.

7. The micro actuator according to claim 1, wherein the flexibility of said second side portion is different from that of said first side portion.

8. The micro actuator according to claim 1, wherein said second side portion is made of wire.

9. The micro actuator according to claim 1, wherein the translationally driving section is motorized.

10. The micro actuator according to claim 1, wherein the driving force of the translationally driving section is rotational force.

11. The micro actuator according to claim 1, wherein the common portion is formed away from the distal end portion.

12. The micro actuator according to claim 1, wherein the amount of enlargement displacement is adjusted by the position of the common point.

13. A micro actuator comprising:

a case;

a translationally driving section having a moving portion mounted on said case for translational movement; and a displacement enlarging member including a first side portion having a first end portion connected to said case, a second side portion having a second end portion connected to said moving portion of said translationally driving section, and a distal end portion, said first and second side portions respectively extending from said first and second end portions and being in direct contact with each other to form a common portion, wherein as said second end portion is pulled on the basis of the translational movement, an amount of displacement of said distal end portion is enlarged more than an amount of the translational movement and said first side portion is elastically bent, said first side portion is made of a material that is different from a material of said second side portion, said first side portion has a hole in the vicinity of a distal end thereof, and a distal end of said second side portion is hooked in said hole.

14. The micro actuator according to claim 13, wherein said second side portion is made of ceramic.

15. The micro actuator according to claim 13, wherein said second side portion is made of glass.

16. The micro actuator according to claim 13, wherein said second side portion is made of wood.

17. The micro actuator according to claim 13, wherein said second side portion is made of wire.

18. The micro actuator according to claim 13, wherein the flexibility of said second side portion is different from that of said first side portion.

* * * * *